(12) United States Patent
Spearman et al.

(10) Patent No.: US 8,945,040 B2
(45) Date of Patent: Feb. 3, 2015

(54) MEDICAL GAS HUMIDIFICATION SYSTEM

(75) Inventors: Michael Spearman, The Woodlands, TX (US); John H. Burban, Lake Elmo, MN (US); Douglas E. Ott, Macon, GA (US); Majid Zia, Saint Paul, MN (US)

(73) Assignee: Lexion Medical LLC, St. Paul, MN (US)

( * ) Notice: Subject to any disclaimer, the term of this patent is extended or adjusted under 35 U.S.C. 154(b) by 0 days.

(21) Appl. No.: 13/507,819

(22) Filed: Jul. 31, 2012

(65) Prior Publication Data

US 2013/0303977 A1 Nov. 14, 2013

Related U.S. Application Data

(60) Division of application No. 12/313,183, filed on Nov. 18, 2008, now Pat. No. 8,292,840, which is a continuation of application No. 10/460,758, filed on Jun. 12, 2003, now Pat. No. 7,476,212.

(51) Int. Cl.

| *A61M 37/00* | (2006.01) |
|---|---|
| *A61F 7/12* | (2006.01) |
| *A61M 13/00* | (2006.01) |
| *A61M 16/16* | (2006.01) |
| *A61M 16/10* | (2006.01) |
| *A61M 16/14* | (2006.01) |

(52) U.S. Cl.
CPC ........... *A61M 13/003* (2013.01); *A61M 16/162* (2013.01); *A61M 16/109* (2014.02); *A61M 16/142* (2014.02)
USPC ............................................. 604/26; 604/113

(58) Field of Classification Search
USPC .......................................................... 604/126
See application file for complete search history.

(56) References Cited

U.S. PATENT DOCUMENTS

| 3,616,796 | A | | 11/1971 | Jackson |
| 4,086,305 | A | | 4/1978 | Dobritz |
| 4,652,408 | A | * | 3/1987 | Montgomery ................. 261/130 |
| 4,708,831 | A | | 11/1987 | Elsworth et al. |
| 5,411,474 | A | | 5/1995 | Ott |
| 5,916,493 | A | * | 6/1999 | Miller ............................ 261/154 |
| 6,068,609 | A | * | 5/2000 | Ott et al. .......................... 604/26 |

* cited by examiner

*Primary Examiner* — Nicholas Lucchesi
*Assistant Examiner* — Weng Lee
(74) *Attorney, Agent, or Firm* — Jacobson & Johnson LLC

(57) ABSTRACT

An apparatus and method for on-the-go humidifying an insufflation gas through water vapor transfer from a liquid to the insufflation gas through a barrier separating the gas from the liquid to enable the gas in a normally trauma inducing state to be brought to a conditioned state. If the gas is at an improper insufflation temperature the temperature of the gas can be brought to the proper insufflation temperature at the same time the gas is humidified through heat transfer through the barrier.

3 Claims, 6 Drawing Sheets

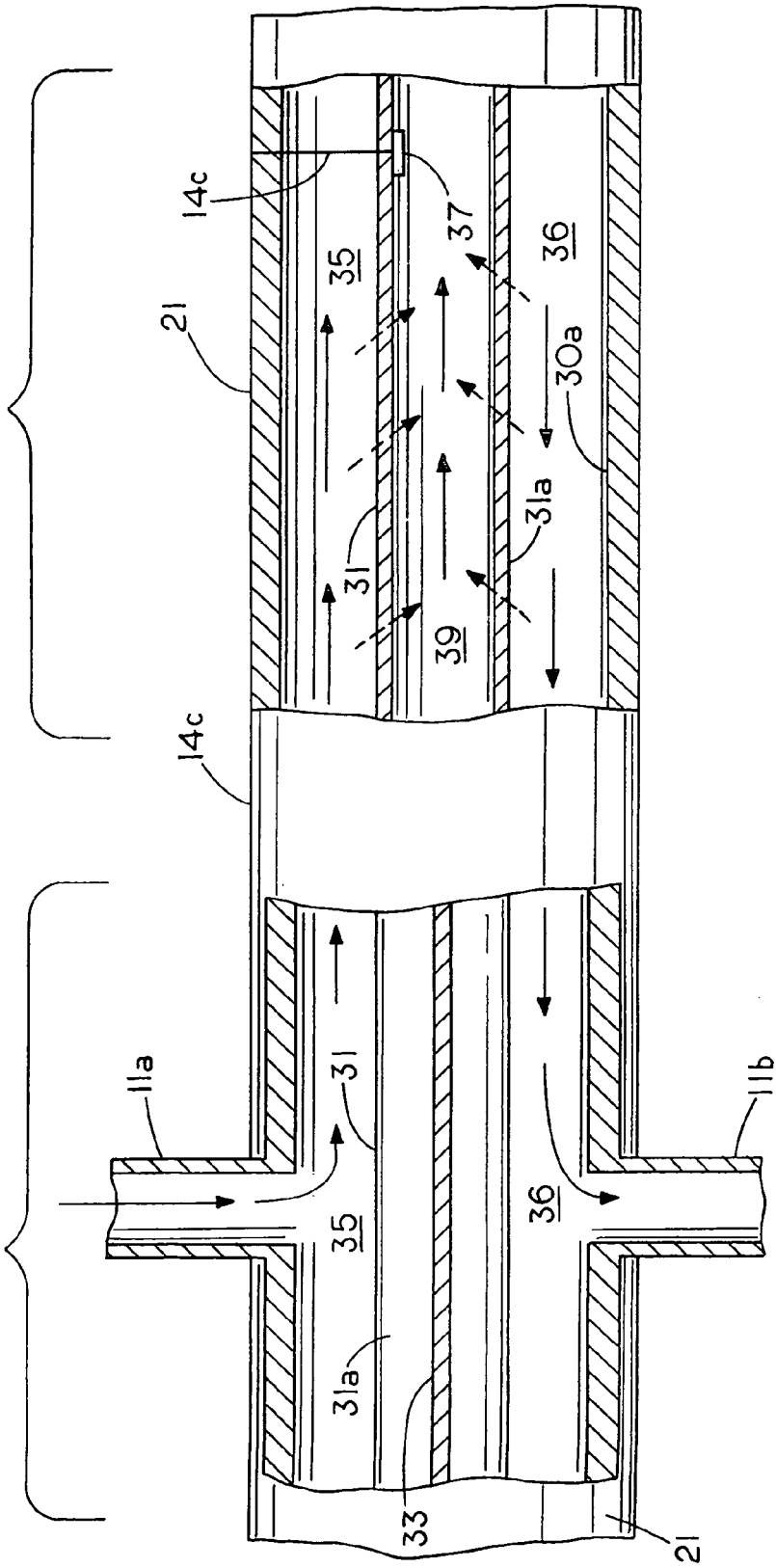

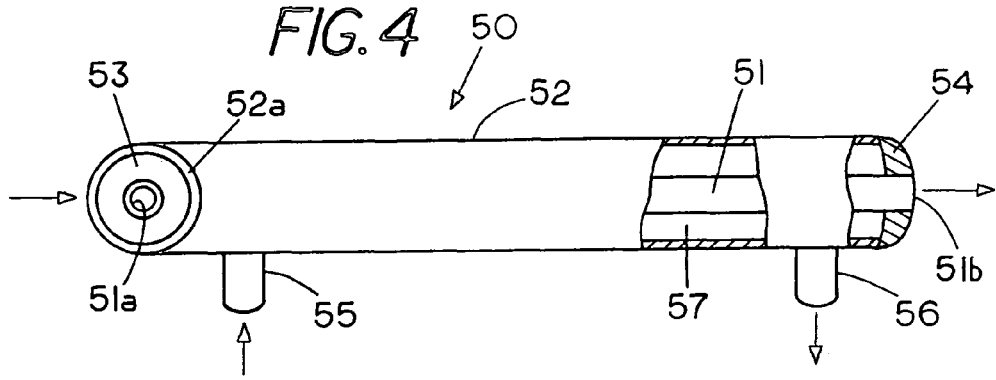
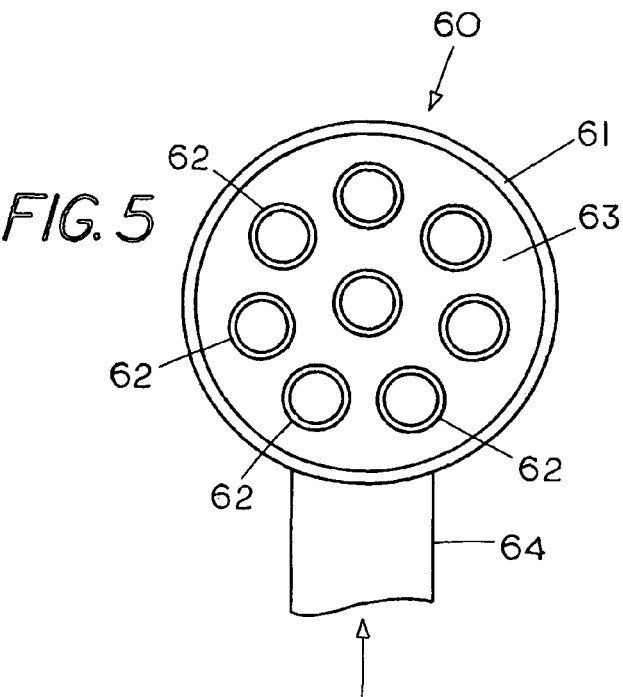
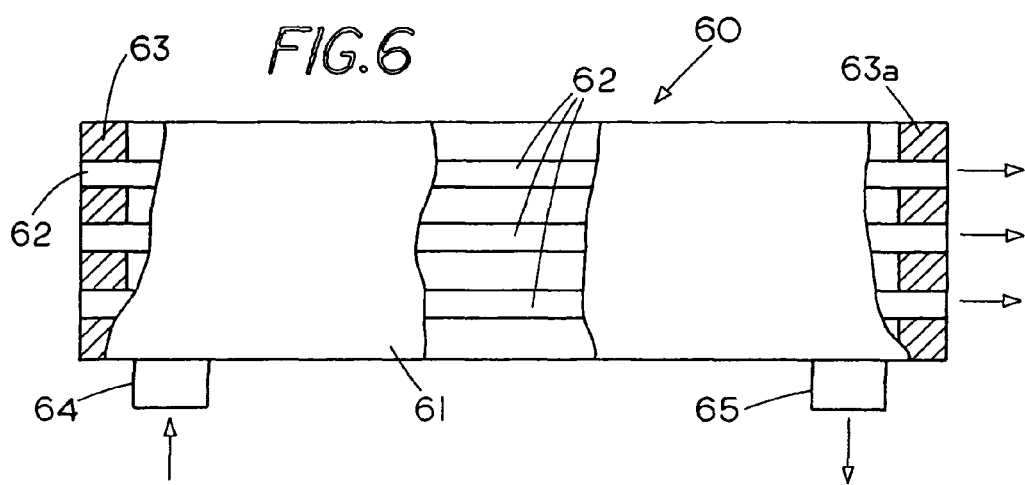

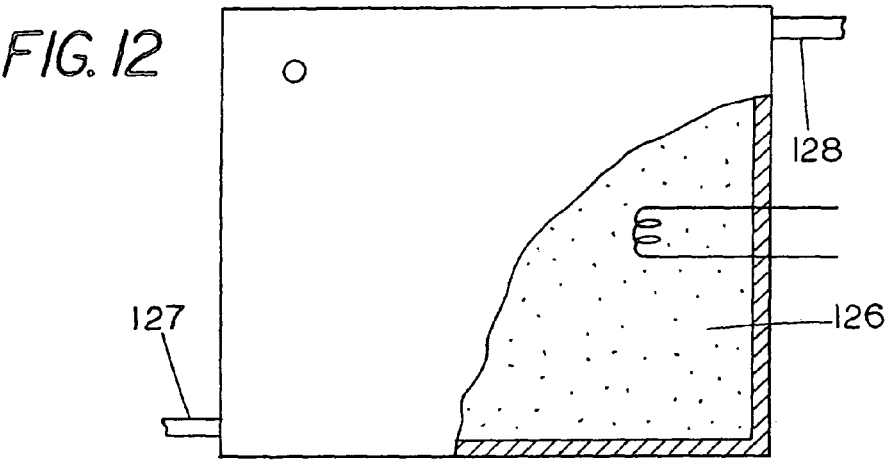
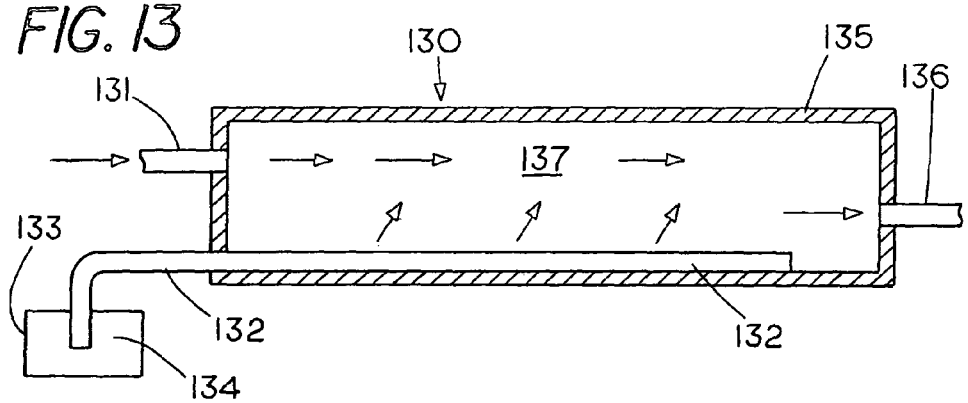
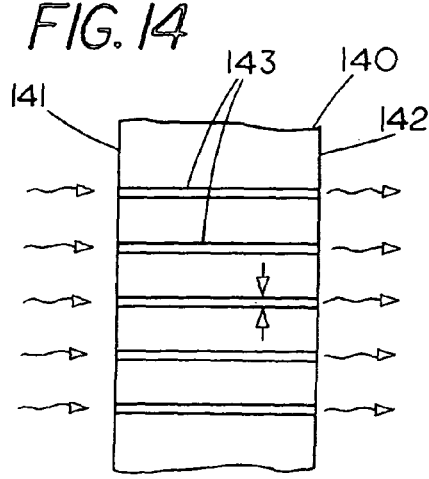
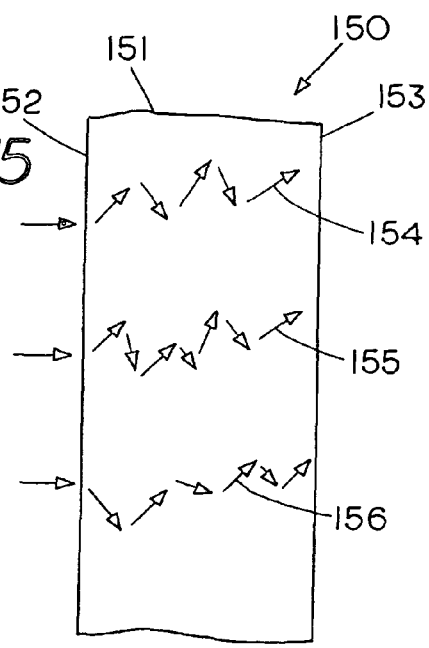

MEDICAL GAS HUMIDIFICATION SYSTEM

CROSS REFERENCE TO RELATED APPLICATIONS

This application is a divisional application of application Ser. No. 12/313,183 filed on Nov. 18, 2008 now U.S. Pat. No. 8,292,840 titled MEDICAL GAS HUMIDIFICATION SYSTEM, which is a continuation application of application Ser. No. 10/460,758, filed Jun. 12, 2003 (now U.S. Pat. No. 7,476,212).

FIELD OF THE INVENTION

This invention relates generally to a medical apparatus and method and, more specifically, an apparatus and method for conditioning a gas so that when the conditioned gas is delivered to a body cavity it prevents or minimizes additional trauma to a patient's body then if the gas were not conditioned.

STATEMENT REGARDING FEDERALLY SPONSORED RESEARCH OR DEVELOPMENT

None

REFERENCE TO A MICROFICHE APPENDIX

None

BACKGROUND OF THE INVENTION

One of the problems during surgery occurs when a medical gas, which is used to insufflate a body cavity, produces additional trauma either directly or indirectly to the body. While the body must endure the trauma produced by the surgery, the use of medical gas, which is often referred to as an insufflation gas, can cause additional trauma to the body resulting in cell stress or cell death. The trauma caused by the medical gas is due to the properties or state of the medical gas that is delivered to the body cavity. For example, the temperature of the gas as well as the moisture content of the gas can produce cell desiccation, cell stress, inflammation and cell death which can result in adhesions as well as pain to the patient and consequently a longer recovery time. Ott et al. U.S. Pat. Nos. 5,411,474 and 6,068,609 recognizes that the cause of the additional trauma from if the medical gas is at an improper insufflation temperature or if the medical gas is to dry when the medical gas is delivered to the body cavity.

The Ott et al. U.S. Pat. No. 6,068,609 discloses a device for conditioning the medical gas wherein water is injected into a heater/hydrator to increase the humidity of the gas as well as the temperature of the medical gas.

The Ott et al. U.S. Pat. No. 5,411,474 discloses a further device for heating, humidifying and filtering insufflation gasses prior to and during medical procedures.

The present invention comprises a method and apparatus using a fluid gas separation barrier that permits water vapor and heat transfer therethrough but prevents liquid transfer therethrough to condition a medical gas by bringing the medical gas from a "trauma inducing state", i.e. a state where the gas if introduced into a body cavity will cause cell stress or cell death, to a "trauma free state" i.e. a state where the introduction of the medical gas into a body cavity does not cause damage to the cells of the body.

SUMMARY OF THE INVENTION

An apparatus and method capable of conditioning a medical gas by humidifying the medical gas through transfer of water vapor from a fluid to the medical gas, which is constrained by a barrier, to enable the medical gas, which is normally in a "trauma inducing state" to be conditioned either statically or on-the-go to a "conditioned state" that prevents or inhibits additional trauma to a patient when the gas in the "conditioned state" is introduced into a patient. The gas is brought to the conditioned state through the transfer of water vapor through the barrier, which extends as an interface separating the water and the medical gas. The barrier is permeable to water vapor transfer but prevents liquid water passage therethrough. In addition, if the medical gas is not at the proper delivery or insufflation temperature the medical gas can be brought to the proper deliver temperature by conduction heat transfer through the barrier. The heat transfer and water vapor transfer can either be separately transferred or the barrier can be used to simultaneously transfer both heat and water vapor to bring the medical gas to the proper insufflation condition.

BRIEF DESCRIPTION OF THE DRAWINGS

FIG. 3 shows a cross sectional view of the outer fluid circulation passages with the medical gas tube coaxially positioned therein;

FIG. 3A shows a cross sectional view of both the medical gas conduit and the fluid circulation tube;

FIG. 4 is a cross sectional view of a medical gas humidification and heat exchange tube;

FIG. 5 is an end view of a medical gas humidification and heat exchange tube with multiple gas ports;

FIG. 6 is a partial side view of the medical gas humidification and heat exchange tube of FIG. 4;

FIG. 12 is a partial cross sectional to view of the closed medical gas humidification and heat exchange system of FIG. 11;

FIG. 13 is a medical gas humidification system for increasing the water content of a medical gas through wicking of moisture into the gas;

FIG. 14 is an enlarged portion of a porous barrier for use in medical gas humidification and heat exchange system with the barrier having pores extending through the barrier to permit water vapor to pass therethrough; and FIG. 15 is an enlarged view of a portion of a non porous barrier for use in medical gas humidification and heat exchange systems with the non-porous barrier that permits migration of water vapor through the barrier.

DESCRIPTION OF THE PREFERRED EMBODIMENT

Figure 1:
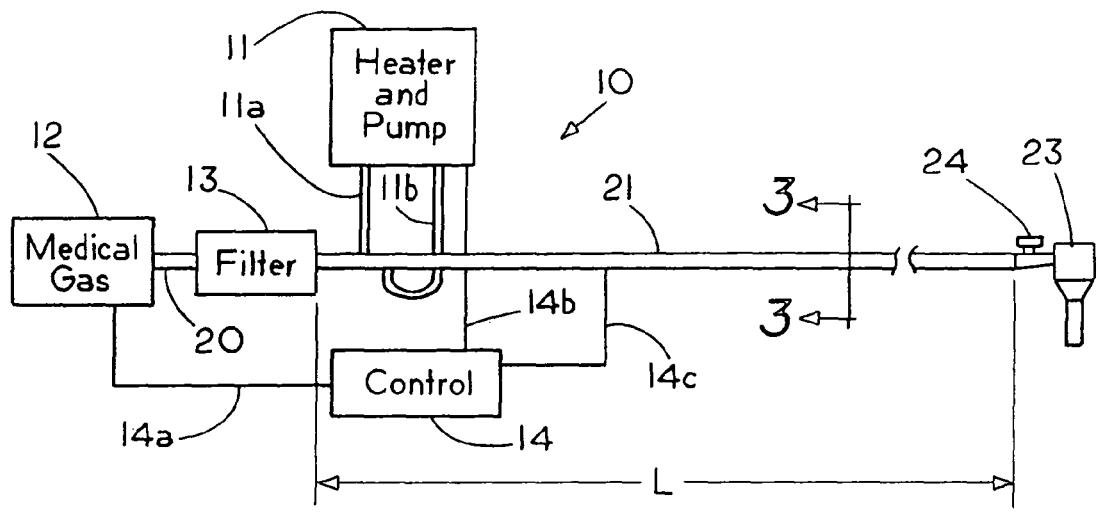
FIG. 1 shows a partial schematic of a system for bringing a medical gas to a trauma free state before delivering the medical gas to a body cavity.

FIG. 1 shows the system 10 of the present invention for either statically or on-the-go delivering a medical gas in a trauma free state. The system 10 includes a source of medical gas 12, a filter 13, which can be used for removing contaminants from the medical gas, and an elongated tube 21 for delivery of the medical gas to an entry device 23. Attached to elongated tube 21 is a heater and pump 11 which circulates a heated fluid through conduit 11a into an elongated flexible tube 21 and then returns the fluid to the heater and pump 11 through conduit 11b. The system is particularly useful in laparoscopic surgery although other types of surgeries requiring insufflation can benefit by the present invention which can prevent peritoneal cell damage, evaporation and desiccation effects.

In the embodiment shown in FIG. 1 a control module 14 connects to the source of medical gas 12 though lead 14a to enable one to control the rate of medical gas flowing into the elongated tube 21 by operation of controls (not shown) in control module 14. Similarly, lead 14b allows one to control the heater and the pump 11 from the control module 14. A third lead 14c extends from a temperature sensor and humidity sensor located proximate the entry device 23 to the control module 14 to permit the operator monitor the medical gas temperature and humidity and through use of the control module set or control the temperature and/or the humidity of the medical gas entering a patient through the entry device 23. A commonly used medical gas which is used for insufflation is carbon dioxide; however, the present invention is usable with other gas including air, nitrous oxide, argon, helium or mixture of gases.

In the system shown, a medical gas under pressure flows through a pressure regulator or insufflator (not shown) and into an elongated tube 21 and into a shutoff valve 24 which has an open and closed condition. With shutoff valve 24 in the closed condition the gas is prevented from entering entry device 23 but with the shutoff valve 24 in the open condition gas flows into entry device 23 which in the present embodiment comprises a trocar sleeve and therefrom into a body cavity of a patient. In order to remove contaminates in the medical gas one can flow the medical gas through filter 13 to remove contaminants therefrom. As the medical gas flows through the elongated tube 21 both heat and water can be transferred to the medical gas to bring the medical gas to a "conditioned state" when it arrives at the entry device 23.

As user herein the "conditioned state" is a gaseous state where the medical gas when introduced into a body cavity limits or inhibits cell stress or cell death due to the contact with the medical gas as opposed to gas in a "non-conditioned state" which can cause additional cell stress and cell death. While the exact conditions of the medical gas that causes cell stress or cell death vary with the person as well as the type of surgery it is understood that at certain humidity and temperature conditions the physical properties of the medical gas causes trauma to the cells of the patient and consequently discomfort or pain to the patient. On the other hand a "conditioned state" is a gaseous state where the medical gas, when introduced into a body cavity, that either does not damage the cells of the body or inhibits damage to the cells of the body as a result of contact with the medical gas in the conditioned state. The conditioned state occurs when the properties of the medical gas are such that the medical gas is at or close to body temperature and the relative humidity of the gas is sufficiently high so as not to produce cell stress or cell death. The exact conditions or properties of the medical gas where the medical gas does not cause cell stress or cell death can vary with the type of tissue as well as many other factors. As used herein, the condition where the delivery of medical gas does not cause stress or damages to the cell is referred to as a condition wherein the medical gas is in a "conditioned state" when introduced into a body cavity. The exact determination of when a gas is in a "conditioned state" can be determined by observation of the effects of a medical gas on the patient; however, such field determination are not feasible since it would cause injury to the patient. Consequently, for most applications maintaining the temperature of the medical gas at or about body temperature and the relative humidity of at the medical gas of least 50% produces medical gas is in a "conditioned state" that can be delivered to the body cavity at either high or low flow rate without causing adverse effects to the patient or the cells of the patients body as a result of contact between the gas and the patient's body. It should be understood, that although the gas in a conditioned state that prevents or inhibits damage to the cells in a patient when the gas is in contact with a patients body the improper delivery of the gas to the patient body cavity can still cause trauma to the patient. However, the present invention provides that with proper delivery of the conditioned gas one can prevent or inhibit additional trauma to a patient. By proper delivery it is understood that the medical gas is brought into contact with the patients body through slow moving gasses to avoid the "wind chill effect".

A reference to FIG. 1 denotes the elongated tube 21 has a transfer length denoted by "L". The distance "L" is the distance along the length of the tube 21 where both heat and water vapor can be transferred between a medical gas located on one side of a liquid gas separation barrier such as a membrane and the fluid located on the other side of the membrane. The barrier of the present invention is permeable to water vapor transfer to permit humidification of the gas on the opposite side of the barrier from the water in the tube 21 while at the same time the barrier prevents liquid water passage through the barrier and into the medical gas. In addition, in the preferred embodiment the separation barrier between the medical gas and the liquid water is formed from a thermally conductive material to enable heat to be transferred between the liquid on one side of the barrier and the gas on the other side of the barrier at the same time water vapor is transferred from one side of the barrier to the other side of the barrier. That is, the heat from a fluid, which is at a higher temperature than the medical gas and normally either above or equal to a normal body temperature (37° C.) is conducted through the barrier to heat the medical gas to the proper insufflation temperature, which in most cases is about normal body temperature as the gas lingers or flows into the transfer tube.

In addition to the heat transfer, water vapor from the fluid diffuses through the barrier to increase the water content or humidity of the medical gas. Thus the barrier or membrane serves a dual function in that it permits heat transfer from the fluid to the medical gas as well as allow diffusion of water into the medical gas from the fluid thereby increasing the humidity of the gas.

Nonporous membranes and porous membranes are known in the art. Typically, nonporous membranes generally comprise polymers that have separation properties based on the relative solubility and permeability of the molecular species of the polymer. Nonporous membranes allow mass transfer to occur thorough a solution diffusion mechanism where a molecule first dissolves into the polymer and diffuses through the polymer from a region of high concentration to a region of low concentration. Since the chemical and physical nature of the molecule affects the solubility and diffusitivity, nonporous membranes can separate mixtures of molecules. Nonporous membranes are typically designed and manufactured to be free of pores that extend through the membrane wall, thus prohibiting a nonselective hydraulic transport of liquid or gasses through the membrane wall. Typical, examples of materials used to form nonporous membranes include polyvinylaccohol, cellulose, cellulose derivatives, nylon, polyesters, polycarbonates, polysulfones, polyethersulfones, polyimides, silicones and polyurethanes. In general, nonporous membranes made from materials that are more permeable to water vapor are preferred since they can reduce the size and cost of the device.

In the present invention one can use a nonporous membrane that permits water molecules to diffuse through the membrane so as to be taken up in a gaseous state yet does not permit liquid water to hydraulically pass through the membrane which would create a gas that contains both a liquid and a gaseous phase and therefore unsuitable for insufflation purposes.

Porous membranes generally have separation properties based on the relative size of the molecules or particles of a mixture. For example, in the present invention one can use a porous membrane that permits water molecules in the gaseous state to diffuse through the pores of the membrane yet does not permit liquid fluids to hydraulically pass thorough the pores of the membrane which could create an insuflation gas that contains both a liquid and a gaseous phase and therefore unsuitable for insufflation purposes. If the pores of the membrane contain gas or water vapor molecules and not liquids this condition is termed in the membrane art as a non-wetting condition.

In operation of a membrane in the non-wetting condition the pores of a non-wetting porous membrane do not become filled with liquid under a pressure differential between the liquid on one side of the membrane and the gas stream on opposite side of the membrane. In the case where the liquid is water, a hydrophobic porous membrane can be used. The degree of hydrophobicity of the membrane is dependent on the size of the pores with membranes of larger pore size requiring materials of lower surface tension. However, to prevent the possible transfer of the bacteria from the liquid steam on one side of the membrane to the gas stream on the opposite side of the membrane a maximum pore dimension of about 0.2 microns is preferred. Typically, materials suitable for the manufacture of a hydrophobic membrane include polyolefins, fluorinated polymers such as tetrafluoroethylene or fluorinated ethylene-propylene, poplyetherimides, polysulfones silicones and other hydrophobic polymers.

While diffusion membranes are described herein other barriers can be formed from materials that permit passage of water vapor therethrough while preventing liquids from passing therethrough can be used. Thus a method and apparatus utilizing a concentration gradient transfer method could be used to transfer the water vapor across a barrier.

Figure 2:
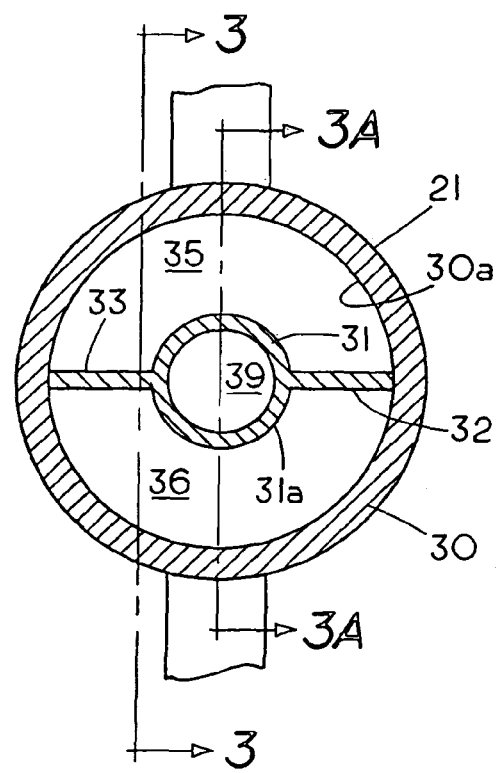
FIG. 2 shows a cross sectional view of one embodiment of the delivery system.

A reference to FIG. 2 shows a cross sectional view of one embodiment of an elongated tube 21. Elongated tube 21 comprises an outer annular member 30 having a central tube 31 located coaxially within tube 21. Central tube 31 is a diffusion membrane that permits water molecules to diffuse therethrough but does not allow for direct flow of fluid therethrough. A first elongated radial fin 32 extends from the exterior cylindrical surface 31a of tube 21 to the interior cylindrical surface 32a of tube 21. Similarly, a second elongated radial fin 33 located diametrically opposite from fin 32 extend from internal cylindrical surface 30a to exterior cylindrical surface 31a of central diffusion membrane 31 to divide the internal lumen of tube 21 into an upper lumen or fluid passage 35 having a generally semi circular cross sectional flow area and a lower lumen or fluid passage 36 also having a generally semi circular cross sectional flow area.

FIG. 3 shows a partial cross sectional view taken along lines 3-3 to reveal the interior fluid passages 35 and 36 of tube 21. Fluids, such as water or in some cases water containing other materials that are to be diffused through the membrane enters fluid passage 35 though the fluid inlet 11a and flows along passage 35 as indicated by the arrows. The tube 31 and the elongated longitudinally extending radial fin 33 and 32 cause the fluid to flow along the exterior semi-cylindrical surface 31a of tube 31 until it is allowed to return along fluid passage 36 which then directs the fluid back to heater and pump 11 through fluid conduit 11b. In order to elevate the temperature of the medical gas to the proper temperature the fluid is heated in heater 11 to a temperature equal or in excess of the desired medical gas temperature to enable conduction heat transfer from the fluid stream in passages 35 and 36 to the medical gas in the central tube 31.

FIG. 3A shows a cross sectional view of a portion of elongated tube 21 in cross section as well as a cross sectional view of internal membrane tube 31, which is a tube with a circular shaped cross section that has been formed from a diffusion membrane. In the embodiment shown the fluid, which is heated by pump and heater 11 flows into fluid passage 35 located along one side of the tube 31 until it reaches the end of the elongated tube 21 where an opening in the radial fin (not shown) allows the fluid to enter fluid passage 36 where it flows along passage 36 until the fluid is directed through outlet port 11b and back into the heater and pump 11. As the fluid flows back and forth along the exterior surface of membrane tube 31 two events occur. First, as the fluid has a higher heat content then the medical gas the gas temperature quickly increases toward the temperature of the fluid in the fluid passages. Second, the membrane tube 31 permits water molecules to diffuse through the sidewall of the membrane tube 31 to increase the gaseous moisture content of the medical gas therein without allowing water or contaminants to flow directly into the medical gas. A temperature sensor/and or humidity sensor 37 is located on the interior of the medical gas conduit 31 with a lead 14c extending therefrom to the control module 14 (FIG. 1) to permit an operator to monitor the temperature and the relative humidity and thus be in a position to control either the temperature of the medical gas delivered to the entry device 23 (FIG. 1) or the humidity of the medical gas delivered to the entry device or both.

In the present invention the inner tube 31 comprises a diffusion membrane that permits diffusion of water vapor from the fluid in chamber 35 into the lumen or gas passage 39 where the medical gas is flowing yet does no permit direct flow of liquid water therethrough which might render the medical gas unsuitable for use. In the present invention, the medical gas is normally at room temperature and is primarily heated by conduction as heat flows from the hotter fluid through the annular member 31 and into the medical gas in gas passage 39 thereby elevating the temperature of the medical gas to an acceptable delivery temperature (usually in the 35° C. to 38° C. range). By simultaneously supplying both moisture and heat to the medical gas one can quickly bring the medical gas to a "conditioned state" before the medical gas discharges from the elongated tube and enters the entry device 23.

In the present invention one can maintain the medical gas in a conditioned state through the use of an extended interface that forms an extended heat transfer region produced by the coaxial positioning of the inner medical gas tube 31 within the interior of outer fluid tube 30.

For various medical procedure there exists a range of flow rates (designated herein by Q) required to maintain a body cavity in an inflated or insufflated condition. In order to maintain the fluid in a "conditioned state" as the gas discharges from the elongated tube 21 and enters the entry device 23, the membrane tube 31 should have an interface region that is sufficiently long and has sufficient transfer area so that there is sufficient heat transfer from the fluid at a maximum flow rate $Q_{max}$ to maintain the temperature of the medical gas at a constant suitable delivery temperature at the entry device 23. That is, as the flow rate Q of medical gases decreases the fluid might require less heat to maintain the medical gas at the proper delivery temperature and conversely at the higher flow rates the medical gas might require more heat transfer to maintain the medical gas at the proper temperature. Thus, through the mechanism of heat transfer, which occurs substantially through conduction, across an extended diffusion membrane 31 one can bring the temperature of the medical gas to an acceptable delivery temperature at the entry device 23 and one can maintain the medical gas at the acceptable delivery temperature even though the flow rate of medical gas through the elongated tube and into the body cavity can fluctuate. Thus, the present invention smoothes out variations in gas delivery temperature since the temperature of the medical gas discharged into the entry device 23 can be maintained at a relative constant acceptable delivery temperature by controlling the velocity and temperature of the fluid flowing in outer fluid passage. If desired, information from the temperature and humidity sensor 37 can be used to automatically control the flow rate of fluid thought a feedback control system.

Similarly, by having sufficient surface area between the fluid stream in lumen 35 and 36 and the medical gas in lumen 39 one can diffuse sufficient moisture into the medical gas to maintain the relative humidity at a minimum level. That is, the elongated tube permits the diffusion of water through the membrane and is sized so that at the maximum flow rate $Q_{max}$ the amount of water that can diffuse through the membranes is sufficient to maintain the relative humidity above a predetermined amount.

While the system has been described as an on-the-go delivery of a medical gas in a conditioned state it will be understood that the system is also usable in those conditions where the on-the-go heating and humidifying of the medical gas is not required.

Thus the invention comprises a system for conditioning a medical gas to bring the medical gas to a conditioned state when delivered to a body cavity with the system including a source of medical gas 12, an elongated coaxial tube 12 having an internal medical gas conduit 31 and a set of exterior semi circular fluid conduits 35 and 36 with the medical gas conduit 31 having a sidewall comprised of a diffusion membrane. The medical gas conduit has an outlet (not shown) for discharging a heated and humidified medical gas into an entry device 23. In order to transfer heat and moisture to the medical gas the fluid passage includes a fluid inlet to the fluid conduit and a fluid outlet in the fluid conduit to permit circulation of the heated fluid to raise the temperature of the medical gas in conduit 31. In order to monitor the state of the gas a medical gas temperature sensor and/or humidity sensor 37 is located on the interior medical gas conduit 31 (FIG. 3A) to monitor the temperature and/or humidity of the medical gas discharging from the medical gas outlet. To maintain the fluid at the proper temperature a pump 11 circulates the heated fluid through an outer fluid conduit so that when the medical gas is delivered through the internal medical gas conduit the fluid circulating through the outer fluid conduit simultaneously raises both the temperature of the medical gas and the humidity of the medical gas to a body deliverable state thorough transfer of both heat and water through membrane 31.

While the present invention discloses a membrane that extends along the length of a cylindrical delivery tube it is envisioned that other shapes interface chambers can be used with the present invention along as there is sufficient membrane interface area to transfer either heat or moisture to the medical gas. As the medical gas is in non-dispersive contact with the water or fluid the membrane prevents transfer of organic or inorganic agents that could contaminate the gas stream. A further benefit of the invention is that the heat and water are distributed more evenly during medical gas flow which can be continuous or intermittent. This results in the gas within the medical gas tube being held at a substantially constant temperature and humidity level even during conditions of no gas flow. In addition, the humidification process is a continuous process since the water is on one side of the membrane and the gas on the other side whether or not either the gas or the water is flowing in the system. A further benefit is that if one wants to maintain the humidity of the medical gas at 100% without condensation the diffusion barrier is self limiting in that water vapor will not transfer through the membrane if the medical gas is saturated with water vapor.

In the present invention both heat and moisture are transferred though the membrane. It is envisioned that if the medical gas is at the proper body delivery temperature one need only use the membrane to transfer moisture into the medical gas.

FIG. 4 is a cross sectional view of an alternate embodiment a medical gas humidification and heat exchange tube 50 that can be inserted into a system to bring the medical gas to the proper delivery state. Tube 50 includes an outer cylindrical tube 52 and an inner cylindrical tube 51 which is centrally held in the lumen of tube 52 by a first annular plug 53 located at one end and a second annular plug 54 located at the other end. The gas tube 51 includes an open end 51a for introducing a medical gas therein. In operation, the medical gas, which can be in an improper insufflation temperature and improper insufflation humidity state, enters tube 51a and flows through tube 51 and discharges at end 51b (indicated by arrows). When the medical gas is discharged from tube end 51b the medical gas is at the proper insufflation temperature and the proper insufflation humidity.

The humidification of the medical gas in tube 51 is accomplished though diffusion of water vapor through the annular barrier wall of tube 51. That is, located around the gas tube 51 is a fluid chamber 57 having an inlet 55 at one end and an outlet 56 at the other end. In the embodiment shown the water entering inlet 55 is at the desired delivery temperature of the medical gas. As the medical gas flows along gas duct 51 water vapor and heat transfer occurs. The humidity or moisture content of the medical gas can be increased to the proper level while at the same time the medical gas can be heated or cooled to the desired delivery temperature at gas outlet 51b through conductive heat transfer through the barrier wall of tube 51.

FIG. 5 is an end view of an alternate embodiment of a medical gas humidification and heat exchange tube 60 which is similar to the heat and humidification tube of FIG. 4 except the heat and humidification tube 60 instead of having a single central gas port has multiple gas ports 62 located in a lumen 63 with the fluid passage formed by the exterior surfaces of the gas ports 62 and the inner cylindrical surface of conduit 61.

FIG. 6 is a partial side view of the medical gas humidification and heat exchange tube 60 of FIG. 5 revealing the end plugs 63 and 63a supporting the multiple gas ducts or tubes 62 therein while gas flows therethrough. The sidewalls of the tubes 62 comprise a barrier to that prevents passage of liquid water into the stream of medical gas in tubes 62 yet permit passage of water vapor therethrough. In operation, the medical gas humidification and heat exchange tube 60 is connected to a source of medical gas on the inlet end and to a device such as entry device on the opposite end.

Figure 7:
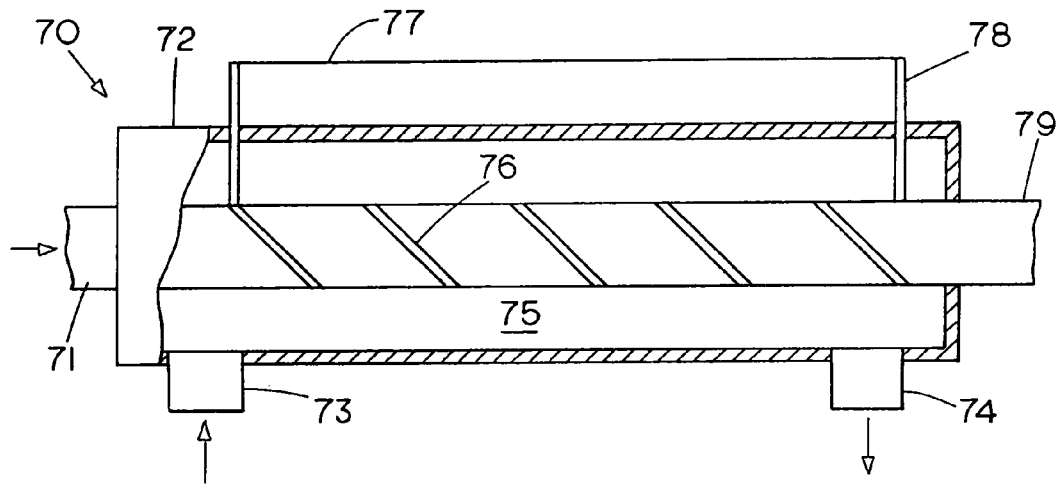
FIG. 7 is a cross sectional view of the medical gas humidification and heat exchange tube with a heating element located on an exterior surface of a central gas duct.

FIG. 7 is a cross sectional view of the medical gas humidification and heat exchange tube 70 having a resistance heating element 76 located around an exterior surface of a central gas duct 79. The gas duct sidewall comprises a barrier to passage of liquid therethrough but permits transfer of water vapor therethrough to humidify the gas in the gas duct. In the embodiment shown the heating element connects to external electrical leads 77 and 78 which can be connected to a control system to maintain the temperature of the water in the chamber 75 at the proper temperature.

As envisioned with the devices of FIGS. 4-7 one can incorporate the medical gas humidification and heat exchange tube directly into the system between the source of medical gas and the device for delivering the medical gas into the patient.

Figure 8:
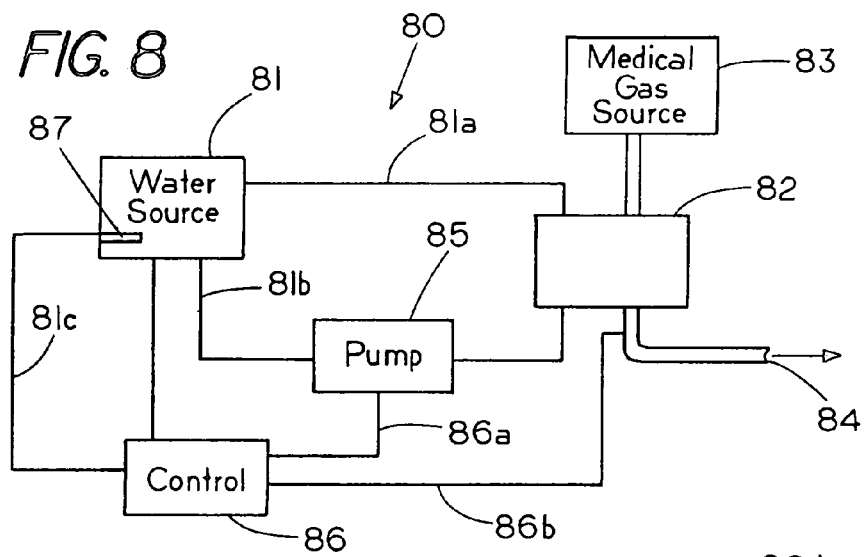
FIG. 8 is a partial schematic diagram of a system for humidifying and heating medical gas.

FIG. 8 is a partial schematic diagram of a system 80 for humidifying and heating medical gas. The system includes a water source 81 with a heating element 87 therein, a medical gas source 83, a heat and moisture exchanger 82, a pump 85 and a control module 86. In operation of the system the pump 85 forces water through passage 81b and directs the water into the heat and moisture exchanger 82. The water then flows in pipe 81a into the water source 81 where the temperature of the water is maintained for recirculation. A control module 86 allows one to increase or decrease the temperature of the water as well as to control the flow rate of the medical gas. The medical gas 83 enters the heat and moisture exchanger 82 wherein heat is transferred to or from the medical gas through conduction and moisture is added to the medical gas through diffusion before the medical gas discharges into the patient though insufflation conduit 84.

Figure 9:
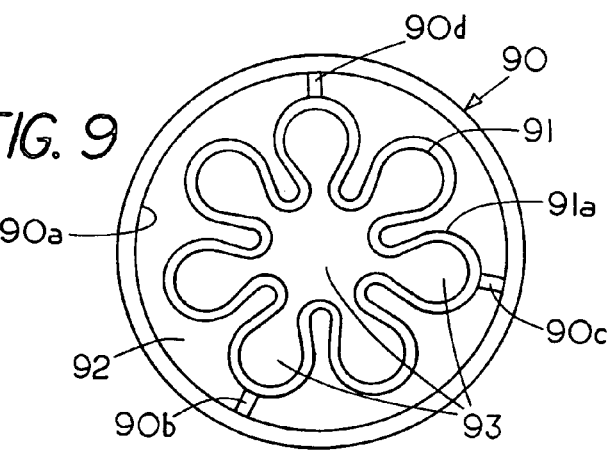
FIG. 9 is an end view of a medical gas humidification and heat exchange tube with multiple passages therein.

FIG. 9 is an end view of an alternate embodiment of a medical gas humidification and heat exchange tube 90 with a daisy like set of multiple radial gas passages 93 formed by an inner fluid conduit 91. The embodiment of FIG. 9 provides a larger surface area between the two fluids per unit length to enable more rapid transfer of heat and water vapor therethrough. Fluid conduit 91 is formed from a material that is a barrier to liquid passage but permits water vapor transfer therethrough. In the embodiment shown in FIG. 9 the inner conduit 91 can be centrally supported by radial struts 90a, 90b and 90c. In operation the embodiment of FIG. 9 a fluid such as water can flow in the passage 92 located between inner surface 90a and outer surface 91a and the insufflation gas can flow in the radial gas passages 93. The fluid can be used as the heat source as well as the water vapor source to transfer heat to and from the medical gas in the radial gas passages 93 to bring the medical gas to the proper insufflation temperature (about 37° C.). Although the central lumen 93 is shown as the insufflation gas passage it is envisioned that the outer lumen 92 could also be used as the insufflation gas passage and the inner conduit used as the fluid transfer conduit. Such an arrangement is well suited to those application where only water vapor transfer across the barrier is required to bring the insufflation gas up to the desired humidification level.

Figure 10:
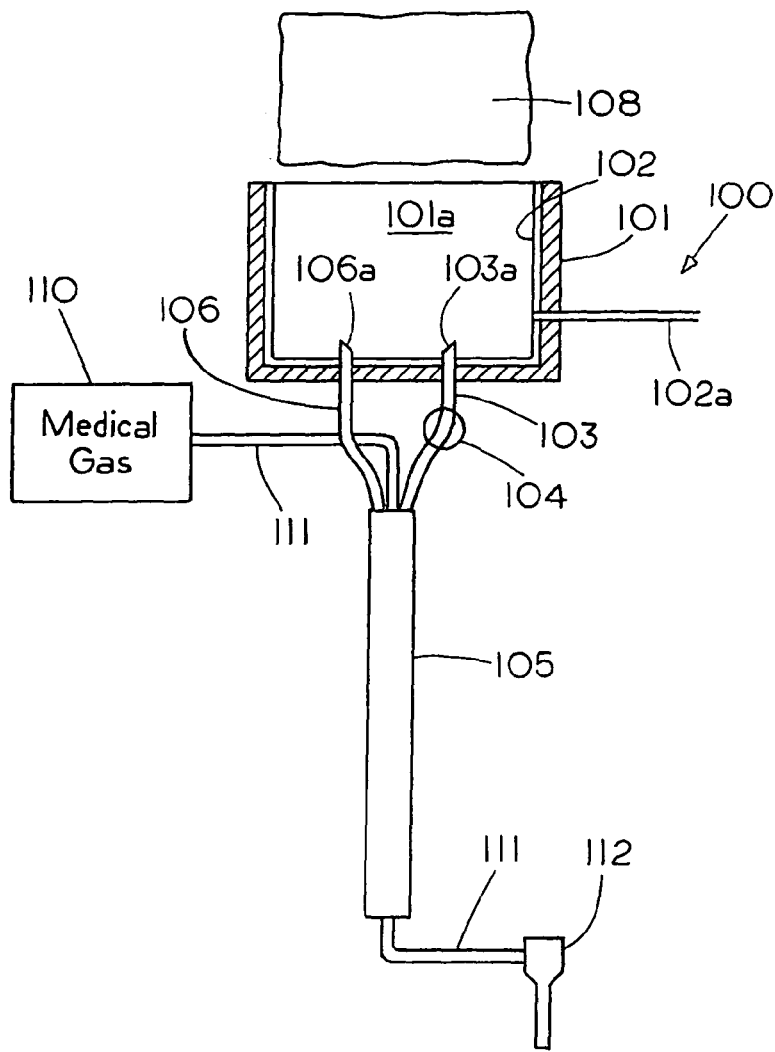
FIG. 10 is a system for delivering a medical gas to an entry device with the system including a chamber with a heating element for heating a container of water placed in the chamber of the system.

FIG. 10 is an alternate embodiment of system 100 using a heat and humidification exchange tube 105. In system 100 a medical gas at proper temperature and humidity is delivered to an entry device 112 with the system including a chamber 101 with a heating element 102 for heating a container of water 108 which is placed in the chamber 101a. In the embodiment shown a sealed pouch 108 containing a fluid is placed in chamber 101a. A first tube 106 having a pointed pouch piercing end 106a and a second tube 103 having a pointed pouch piercing end 103a projects upward into the chamber 101a. In operation of the system a flexible skin pouch or other type of punctureable container 108 is forced onto the pointed ends 106a and 103a causing penetration of the container 108. The container can be made of resilient material that seals around itself as the pouch is punctured. Once the tubes 103a and 106a are inserted in the pouch the fluid can be circulated to and from the pouch through tubes 103 and 104.

Tube 103 connects to the medical gas humidification and heat exchange tube 105. A pump 104, which could be a peristaltic type pump, draws fluid into tube 103 and forces fluid out tube 106. The medical gas source 110 delivers the medical gas to the medical gas humidification and heat exchange tube 105 through passage 111. The medical gas humidification and heat exchange tube 105 brings the temperature of the gas to the proper deliver temperature by conduction heat transfer through a sidewall of a gas passage and to proper humidity by transfer of water vapor through the sidewall of the gas passage.

Figure 11:
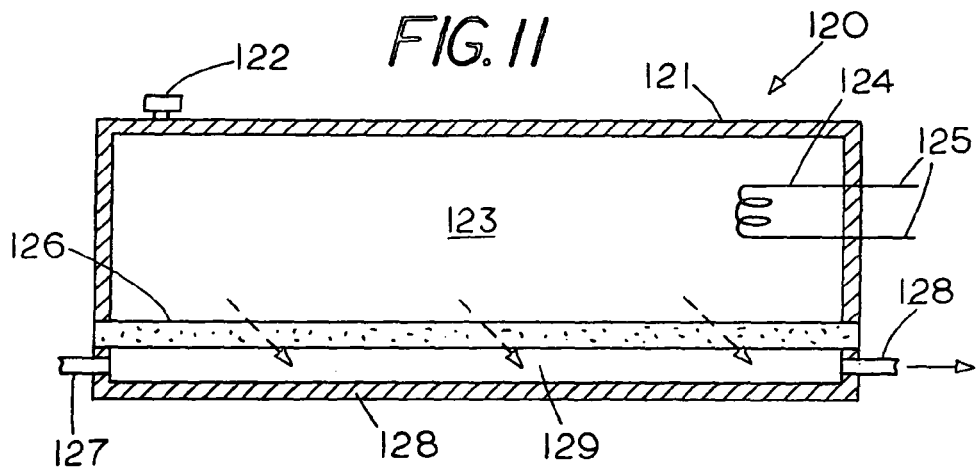
FIG. 11 is a cross sectional side view of a closed medical gas humidification and heat exchange system.

While the embodiments of the heat and humidification exchange members are shown as tubes, FIG. 11 and FIG. 12 show a cross sectional side view of another embodiment of a medical gas humidification and heat exchange system 120. System 120 comprises a housing 121 having a water vapor permeable member 126 forming the bottom of a fluid chamber 123. Located in fluid chamber 123 is a heating element 124 that has electrical leads 125 that extend outward for connection to a source of electrical power. A vent cap 122 allows one to fill the chamber 123 with a fluid such as water. Located below water vapor permeable member 126 is a gas chamber 128 having an inlet 127 and an outlet 128. In the embodiment shown the large volume of the fluid chamber 123 and the medical gas chamber permit continuos heat and moisture transferred to the medical gas throughout the surface area of the barrier 126 that separates chamber 124 from chamber 129. In this embodiment the moisture and heat transfer is accomplished through the use of a flat compact barrier or the like as opposed to an elongated tube.

FIG. 13 is a medical gas humidification system 130 for increasing the water content of a medical gas through wicking of moisture into chamber 137 followed by evaporation into the gases state. System 130 includes a closed chamber 135 having a medical gas inlet 131 and a medical gas outlet 136 with a chamber 137 located in the enclosure. A wick 132 extends through the wall and into a container 133 having water 134 therein. In operation of the system shown in FIG. 13 the medical gas enters the chamber 137 and the moisture in wick 132 is picked up by the medical gas before it is discharged from housing 135. In this embodiment the medical gas can be brought to the proper temperature before it enters the system 130. An advantage of this type of wick system, particularly when positioned proximate the point of entry into the patient, is that if the gas is cooled slightly as it enters the patient any moisture condensation can be absorbed by the wick rather than being carried into the patient as liquid droplets. Thus if the temperature of the medical gas is at the proper temperature the wick system of FIG. 13 can be used to provide moisture to the medical gas or to remove any condensed liquid. As an alternate the system 130 can be used in conjunction with a heat and exchange tube described herein that may be located a distance from the patient since the wick can absorb and prevent liquid droplets from entering the patient if any moisture condenses out of the medical gas as it enters the patient.

Although a permeable membrane has been described for the transfer of moisture other liquid barriers that permit water vapor transfer can be used. FIG. 14 is an enlarged portion of porous barrier 140 for use in medical gas humidification and heat exchange system with the barrier having micro pores 143 extending from side 141 of the barrier to opposite face 142 to permit water vapor to pass therethrough.

FIG. 15 is an enlarged view of a non porous barrier 150 for use in medical gas humidification and heat exchange systems with the non-porous barrier that permits migration of water vapor through the barrier yet there are no direct openings in the barrier. Porous barrier 151 has a first face 152 and a second face 153 which forms a liquid barrier. A set of arrows 154 155 and 156 are shown in a zig zag pattern to illustrate the passing of water vapor from face 152 to face 153.

Thus the present invention includes a method of delivering a medical gas in a conditioned state to a body cavity to avoid or inhibit body trauma by directing a medical gas into a body cavity through a lumen located on a first side of a barrier permeable to water vapor but impermeable to liquid water to thereby transfer water vapor through the barrier and into the medical gas so that when the medical gas discharges therefrom the humidity of the medical gas is in a conditioned state for insufflation.

In an alternate embodiment the invention includes an apparatus for delivering medical gas in a conditioned state to a body cavity with the system including, a medical gas; a chamber for holding the medical gas; a source of water located external the chamber for holding the medical gas and a wick extending into the source of water and into the chamber to permit the wicking of water into the medical gas located therein to bring the medical gas to the proper insufflation humidity.

We claim:

1. An apparatus for delivering medical gas in a conditioned state to insufflate a body cavity during a surgical procedure comprising:
 a medical insufflation gas;
 a housing having a closed chamber for holding the medical insufflation gas;
 a medical gas inlet for introducing an unhumidified medical insufflation gas into the chamber with the medical gas inlet located at a first end of said closed chamber, said medical gas inlet orientated in a first direction to direct the unhumidifed gas in a first flow direction into the closed chamber to form a medical insufflation gas flow path from the first end of the closed chamber to a second end located at an opposite end of the closed chamber, said medical insufflation gas brought to a proper temperature prior to entering the chamber,
 a medical gas outlet located at the opposite end of the closed chamber with said medical gas outlet orientated in the first direction for receiving and delivering a humidified medical insufflation gas along the first direction;
 a source of water, said source of water located external to the chamber for holding the medical insufflation gas;
 a wick extending through a wall of said housing with said wick having a first portion extending alongside a first internal wall of the housing and proximate the flow path through said closed chamber and a second portion outside the closed chamber with a first end of said wick located outside said chamber and a second end of said wick located within said chamber with said first end of said wick extending into said source of water to permit the wicking of water from the outside of the chamber to the inside of the chamber where the medical insufflation gas located therein can pick up moisture from the wick as the medical gas flows alongside the wick and end to end of the housing or absorbs any moisture condensation of the medical insufflation gas before the moisture condensation can be carried into a patient.

2. The apparatus of claim 1 wherein the wick comprises a flexible fabric.

3. The apparatus of claim 1 wherein the wick is located proximate a point of entry into the body cavity to be insufflated so that the moisture condensation can be absorbed by the wick to thereby prevent ingress of the moisture condensation into the body cavity of the patient.

* * * * *